United States Patent [19]
Sugisawa et al.

[11] Patent Number: 5,866,514
[45] Date of Patent: Feb. 2, 1999

[54] PESTICIDAL COMPOSITION TO NOXIOUS ORGANISMS

[75] Inventors: Kunio Sugisawa, Yokohama; Yasuo Togami, Kisarazu; Toshikatsu Shouko, Kawasaki, all of Japan

[73] Assignee: Nippon Petrochemicals Company, Limited, Tokyo, Japan

[21] Appl. No.: 676,662

[22] Filed: Jul. 10, 1996

[30] Foreign Application Priority Data

Jul. 11, 1995 [JP] Japan .................................. 7-197974

[51] Int. Cl.$^6$ ........................ A01N 29/12; A01N 33/18; A01N 47/10; A01N 57/00
[52] U.S. Cl. ........................ 504/347; 504/116; 514/86; 514/89; 514/112; 514/132; 514/136; 514/147; 514/148; 514/479; 514/481; 514/748
[58] Field of Search ................ 514/86, 89, 136, 514/147, 479, 481, 748, 112, 132, 148; 504/347, 116

[56] References Cited

U.S. PATENT DOCUMENTS

| | | | |
|---|---|---|---|
| Re. 31,927 | 6/1985 | Coffee et al. ............................ | 514/521 |
| 4,737,520 | 4/1988 | Naik et al. .............................. | 514/520 |
| 4,760,084 | 7/1988 | Ohtsubo et al. ........................ | 514/521 |
| 4,871,766 | 10/1989 | Tsuda et al. ........................... | 514/521 |
| 4,886,656 | 12/1989 | Obayashi et al. ....................... | 424/10 |

FOREIGN PATENT DOCUMENTS

| | | |
|---|---|---|
| 0 229 372 A1 | 7/1987 | European Pat. Off. . |
| 56-19841 | 5/1981 | Japan . |
| 58-14401 | 3/1983 | Japan . |

OTHER PUBLICATIONS

Kirk–Othmer *Encyclopedia of Chemical Technology,* vol. 2, 1978, pp. 50, 61–62.

*Primary Examiner*—Allen J. Hubinson
*Attorney, Agent, or Firm*—Fisher, Christen & Sabol

[57] ABSTRACT

A pesticidal composition to noxious organisms which comprises a diarylalkane and an active component effective for killing or repelling noxious organisms and the diarylalkane is at least one member selected from the group consisting of butyl diphenylmethane, butyl-1,1-diphenylethane and butyl-1,2-diphenylethane. The used diarylalkane has a high dissolving power to the effective component, a high boiling point and a high flash point with low unpleasant smell and does not deteriorate the effective component in the pesticidal composition.

12 Claims, 1 Drawing Sheet

PESTICIDAL COMPOSITION TO NOXIOUS ORGANISMS

BACKGROUND OF THE INVENTION (1) Field of the Invention

This invention relates to pesticidal compositions such as insecticide, germicide, repellents and herbicide which are used for repelling or killing noxious organisms. In other words, the term "pesticidal composition" includes the composition that keeps noxious organisms away or kills them to prevent their attack.

(2) Description of Prior Art

The pesticidal composition to noxious organisms such as agricultural chemicals are used in various forms of preparations. The forms of compositions are exemplified by solid forms such as powder, powdery granules, granules, hydrated preparations and pills; liquid forms such as solutions, emulsions, oily preparations and flowable preparations; and aerosols, coating compositions, gaseous agents, smoking agents and microcapsules. In a microcapsule-type preparation, an effective component is encapsulated with a high polymer membrane or thin sheets of effective component are sandwiched between layers of polymer.

More particularly, the powdery composition is prepared through a process such that an effective component is mixed with powder of clay mineral such as talc or bentonite, and the mixture is then pulverized into fine powder of about 10 μm in average diameter. This can be used intact by spreading with a sprayer. The DL powder in which the drifting is minimized by removing very fine powder having a particle size smaller than a certain value and flow dust (FD) composition for use in gardening fall under the above-mentioned category. The powdery granules are prepared by using clay powder which has a particle size larger than that of the above powdery composition. The granular composition is a solid preparation of medium-sized particles of a value between those of the above powdery composition and the powdery granules.

The hydrated composition is prepared by adding a clay mineral, surface active agent and diluent to an effective component which is hardly soluble to water, thereby forming a powdery solid. When this composition is used, a suitable quantity of water is added to prepare a suspension and the prepared suspension is sprayed. Further-more, exemplified as the compositions belonging to this category are the hydrated tablets (dry flowable pills) having a larger particle size and a water soluble composition which is prepared by adding an auxiliary component to a water soluble effective component.

The liquid composition is a concentrated solution of an effective component which is prepared by dissolving the effective component into a suitable volatile solvent. The liquid composition is also exemplified by an emulsion and an oily composition. The emulsion is prepared by emulsifying an effective component in water or in an organic solvent with a surface active agent. The oily composition is prepared by dissolving an effective component into an organic solvent. Both of them can be used by diluting with water or with an organic solvent and then spraying or spreading.

The constituents of the above compositions are generally classified into three groups of effective components (chemical agents for killing or repelling noxious organisms), diluents and auxiliary agents. The effective components are the so-called agricultural chemicals. The diluent facilitates the preparation of the pesticidal composition by diluting the effective component properly. The diluents are exemplified by solid diluents (carriers) and liquid diluents. The auxiliary agents are used for imparting several properties such as emulsifiability, dispersibility, spreadability and solubility relative to the effective component, for preventing the effective component from decomposition during storage or after spraying, or for improving the sticking of effective component to farm products. Even when the auxiliary agent itself has no pesticidal effect, those which can enhance the effect of the composition when used together are also included in the category of auxiliary agent. By the way, it is sometimes difficult to distinguish the above-mentioned diluents from the auxiliary agents.

The preparation of pesticidal composition using the liquid diluent or auxiliary agent will be described further.

In the preparation of an oily composition, they are employed as an organic solvent to dissolve the effective component. In the preparation of emulsified composition, a solution of effective component is formed and the solution is emulsified with water. In the case of powder composition and granular composition, an effective component is dissolved in a solvent and carrier particles are coated with the solution or the carrier is kneaded or impregnated with the solution so as to form powder or granular composition.

The organic solvents used for preparing the oily composition and emulsified composition are exemplified by the hitherto used hydrocarbons such as alcohols, ketones, ethers and paraffins; and aromatic hydrocarbons such as benzene, toluene, xylene and dodecylbenzene. Besides these solvents, there are proposed the use of phenyl xylylethane (Japanese Patent Publication No. Sho 56-19841) and compounds having specific structure (Japanese Patent Publication No. Sho 58-14401).

Furthermore, the uses in the preparation of solid compositions are disclosed in U.S. Pat. No. 4,760,084; U.S. Pat. No. 4,871,766 and U.S. Pat. No. 4,886,656.

It is to be noted, however, that the spreading or spraying using phenyl xylylethane as disclosed in Japanese Patent Publication No. Sho 56-19841 is not satisfactory in view of the safety to fire. In order to ensure the safety, the substance having a higher flash point and higher boiling point is desired.

Also concerning the smell, with giving consideration to worker's unpleasant feeling in the spreading or spraying operation, odorless composition having no nasty smell is required. When the pesticidal composition in any form is used to noxious organisms, it is spread or sprayed in large quantities over fields, farms, fruit farms, forests, lumber, houses and so forth. Therefore, it is necessary to use odorless composition in view of the prevention of environmental pollution.

BRIEF SUMMARY OF THE INVENTION

It is, therefore, the primary object of the present invention to provide a pesticidal composition to noxious organisms which comprises a diarylalkane having the following general formula [I] and an effective component (active agent) for killing or repelling noxious organisms:

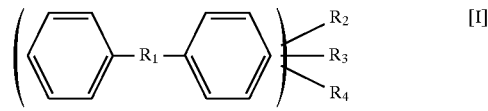

wherein $R_1$ is a bivalent radical which is formed from methane or ethane, each of $R_2$ and $R_3$ is a hydrogen atom or an alkyl group having 3 or 4 carbon atoms, $R_4$ is an alkyl group having 3 or 4 carbon atoms, and the groups $R_2$, $R_3$ and $R_4$ can be the same or different ones.

The second object of the present invention is to provide the pesticidal composition to noxious organisms in which the diarylalkane in the above first object is any one member selected from the group consisting of butyl diphenylmethane, butyl-1,1-diphenylethane and butyl-1,2-diphenylethane.

The third object of the present invention is to provide the pesticidal composition to noxious organisms in which the diarylalkane of the above first object is a mixture of 20 to 80 wt. % of butyl diphenylmethane, 5 to 50 wt. % of butyl-1,1-diphenylethane and 5 to 50 wt. % of butyl-1,2-diphenylethane.

The fourth object of the present invention is to provide the pesticidal composition to noxious organisms in which more than 80 wt. % of butyl diphenylmethane is contained.

BRIEF DESCRIPTION OF THE DRAWING

These and other objects and features of the invention will become more apparent from the following description taken in connection with the accompanying drawings in which.

DETAILED DESCRIPTION OF THE INVENTION

Figure 1:
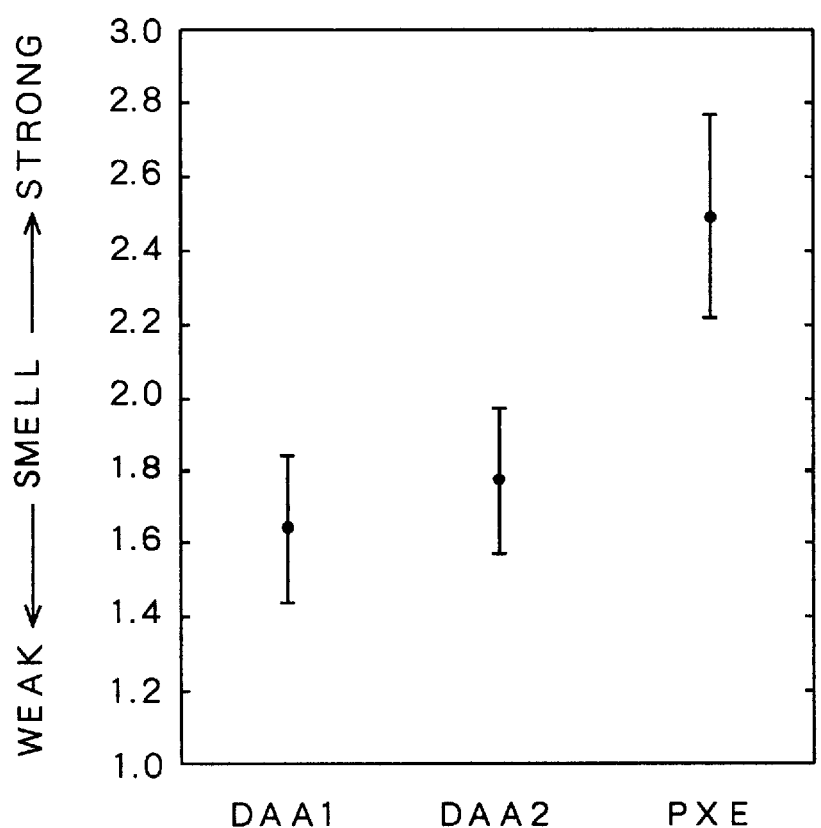
FIG. 1 is a graphic chart of test results concerning the comparison of smell of diarylalkanes.

Because the effective component of the pesticidal composition contains many polar groups, the compound having benzene nucleus readily dissolves the effective component. However, the quality and the intensity of smell depend upon the molecular weight of a compound. In other words, in the diarylalkane of the above-mentioned formula [I], when the numbers of carbon atoms in the alkyl groups are increased, the molecular weight is increased, so that the quality and intensity of smell are made better and the flash point is raised to provide a safer compound. However, the dissolving power relative to an effective component is large if the aromaticity (the ratio of benzene ring carbon relative to the whole number of carbons in a molecule) is large. Accordingly, the increase in molecular weight invites a tendency which is contrary to the former case.

In the present invention, with giving consideration to the balance between both instances, the radicals in the diarylalkane of the formula [I] are defined as follows. That is, $R_1$ is a bivalent group which is formed from methane or ethane, each of $R_2$ and $R_3$ is a hydrogen atom or an alkyl group having 3 or 4 carbon atoms, $R_4$ is an alkyl group having 3 or 4 carbon atoms, and the groups R2, $R_3$ and $R_4$ can be the same or different ones.

More particularly, the substituent groups of $R_2$, $R_3$ and $R_4$ are exemplified by n-propyl, isopropyl, n-butyl, sec-butyl, isobutyl and tert-butyl groups.

The diarylalkanes used in the present invention have high boiling points, high flashing points and low vapor pressures, so that the safety relative to fire is high. In addition, the harmful effect is small in spreading and spraying operation because the ill odor and irritation are not intense. Especially, the diarylalkanes used in the present invention are weak-smelling and, even when any kind of smell is sensed or felt, it is not an unpleasant smell. Furthermore, the decomposition or deterioration of effective component is not caused to occur in the solution of the component, so that the degree of deterioration in repelling or killing effect with the passage of time in use is small. Still further, the coloring (browning) hardly occurs in the dissolving of effective agent.

The above diarylalkanes of the formula [I] are exemplified by propyl diphenylmethane, propyl-1,1-diphenylethane, propyl-1,2-diphenylethane, butyl diphenylmethane, butyl-1,1-diphenylethane, butyl-1,2-diphenylethane, dipropyl diphenylmethane, dipropyl-1,1-diphenylethane, dipropyl-1,2-diphenylethane, dibutyl diphenylmethane, dibutyl-1,1-diphenylethane and dibutyl-1,2-diphenylethane. These compounds can be used singly or as a mixture of them.

Especially preferable diarylalkanes are butyl diphenylmethane, butyl-1,1-diphenylethane, and butyl-1,2-diphenylethane. As butyl groups, any one of n-butyl, sec-butyl, isobutyl and tert-butyl groups can be used, however, the sec-butyl group is preferable. The diaryl-alkane having substituents of sec-butyl groups has a relatively low viscosity to facilitate the handling, so that the sec-butyl group is desirable as a substituent group. Accordingly, the most preferable diarylalkanes are sec-butyl diphenylmethane, sec-butyl-1,1-diphenylethane and sec-butyl-1,2-diphenylethane.

As described in the foregoing paragraphs, the diarylalkanes of the formula [I] according to the present invention can be used either singly or in combination of two or more. In view of the synergistic effect that the pour point can be lowered and the production cost can be reduced, the composition of the present invention is preferably a mixture of a plurality of diarylalkanes including their isomers.

From this point of view, the mixture of butyl diphenylmethane, butyl-1,1-diphenylethane, and butyl-1,2-diphenylethane is preferable and the mixing ratios of them are in the ranges of 20 to 80 wt. % of butyl diphenylmethane, 5 to 50 wt. % of butyl-1,1-diphenylethane and 5 to 50 wt. % of butyl-1,2-diphenylethane.

Because the sec-butyl group is preferable as the substituent group as described above, the more preferable mixture of diarylalkanes is the mixture of 20 to 80 wt. % of sec-butyl diphenylmethane, 5 to 50 wt. % of sec-butyl-1,1-diphenylethane and 5 to 50 wt. % of sec-butyl-1,2-diphenylethane.

In the case that a higher dissolving power to an effective component is required, the mixture containing much butyl diphenylmethane is desirable. That is, if the dissolving power is regarded as an important factor, the diarylalkane mixture may preferably contain more than 80 wt. % of butyl diphenylmethane. Because the sec-butyl group is preferable as the substituent group as described above, the more preferable mixture of diarylalkanes is the mixture containing more than 80 wt. % of sec-butyl diphenylmethane.

In the mixing ratios herein referred to, the total quantity of diarylalkanes as represented by the foregoing formula [I] is 100 wt. %.

The compounds as represented by the formula [I] used in the present invention can be prepared by any method which has been known in the conventional art. In the following, the method for producing butyl diphenylmethane, butyl-1,1-diphenylethane and butyl-1,2-diphenylethane will be described.

There are several methods that diphenylmethane, 1,1-diphenylethane or 1,2-diphenylethane is alkylated with an alkylating agent such as butene or butylchloride in the presence of an acid catalyst; butylbenzene is benzylated with aralkylating agent such as benzyl chloride or benzyl alcohol; trans-aralkylation of butylbenzene and diphenyl-methane or diphenylethane; and coupling of benzene and butyl-benzene with dichloromethane.

Exemplified as the methods for obtaining a mixture of two or more kinds of butyl diarylalkanes are a method in which predetermined quantities of diphenylmethane, 1,1-diphenylethane and 1,2-diphenylethane are previously mixed and the mixture is then subjected to alkylation or a method in which butyl diphenylmethane, butyl-1,1-diphenylethane and butyl-1,2-diphenylethane are previously synthesized and they are mixed together.

In the present invention, when the diarylalkane of the formula [I] is used, various solvents which are well known in the conventional art can be used. Such solvents are exemplified by solvents such as alcohols, ketones, ethers, paraffins and naphthenes; aromatic hydrocarbon such as benzene; alkylbenzenes such as toluene, xylene and dodecylbenzene; alkylnaphthalene such as isopropylnaphthalene; alkylbiphenyl such as isopropylbiphenyl; aromatic solvents having aromatic rings such as aromatic alcohols, ketones and ethers; or diarylalkanes other than those represented by the foregoing formula [I] such as phenylxylylethane, benzyltoluene and dibenzyltoluene. These solvents can be used by mixing in any ratio.

The effective components of the pesticidal composition which are used together with the diarylalkanes of the formula [I] in the present invention, include a germicide, insecticide, herbicide, anti-epidemics, and other chemicals such as formicide, rodenticide, incentive agent, repellent and the like so as to repel or kill germs which are noxious to trees, forestry or to repel or kill and farm products, insects, ticks, eelworms, mice, insanitary worms, noxious worms, weeds, other undesirable animals, plants and virus. Furthermore, the effective components of the pesticidal composition of the present invention also include the agent to control the growth of plants by enhancing or suppressing the physiological activity. Still further, the vermicide for clothing to avoid burs, household vermicide for avoiding insanitary worms such as flies, mosquitos and cockroaches, or noxious vermins such as centipedes and ants, and repellents, fungicides, industrial microbicides, and anti-white ant agents are included.

The active components for the pesticidal composition of the present invention is not restricted to any specific chemical compound. More particularly, the active components are exemplified by vermicides, germicides and herbicides of organic phosphorus types, carbamate types and organic chlorine compound types, and herbicides of phenoxy types, benzoic acid type, phenol type, urea type, dinitroaniline type, nitrile type, S-triazine type, diazine type and the mixture of them. All of them are liquid or solid at ordinary temperatures as the effective components.

Particular vermicides, germicides and formicides are exemplified in the following. The names of effective components are indicated by any one of chemical nomenclature, common name or international standard nomenclature.

Organic phosphorus compounds are exemplified by O,O-dimethyl-O-(3-methyl-4-nitrophenyl)thiophosphate (trade name: Sumithion), ethyl-p-nitrophenyl-phenylphosphorothionate (trade name: EPN), diethyl-2,4-dichlorophenyl)thiophosphate (trade name: VC), dimethyl-4-methylthio-m-tolylphosphorothionate (trade name: Baytex), O,O-diethyl-O-(2-isopropyl-4-methyl-6-pyrimidinyl)phosphorothioate (trade name: Diazinon), O-ethyl-diphenyldithio phosphate (trade name: Hinozan), S-benzyl-ethyl-phenylphosphonothiolate (trade name: Inezin), tetrachlorovinphos (trade name: Guardcide), phoxim (trade name: Varicide), and O,O-dimethyl-O-(2,2-dichlorovinyl)phosphate (DDVP).

Carbamate compounds are exemplified by 1-naphthyl-N-methylcarbamate (trade name: Denapon), 2-(ethylthio-methyl)phenyl-methylcarbamate (trade name: Arylmate) and 2-butylphenyl-N-methylcarbamate (trade name: Vassa).

Organic chlorine compounds are exemplified by O,O-diethyl-O-3,5,6-trichloro-2-pyridyl phosphorothioate (trade name: Chlorpyrifos), tetrachloroisophthalonitrile (TPN), 4,5,6,7-tetrachlorophthalide (trade name: Phthalide), N-tetrachloroethylthiotetrahydro phthalimide (trade name: Daiholtan) and chlorobenzylate (trade name: Akal).

In addition, O,O-diethyl phthalimid methyldithiophosphate (trade name: PMP), etofenprox (trade name: Trebon), and tripropyl cyanate (trade name: Woodlack) are also included.

Furthermore, the effective compounds are exemplified by phenoxy types of sodium-2,4-dichlorophenoxyacetate (trade name: 2,4-D sodium salt) and sodium[(4-chloro-o-tolyl)oxy]acetate (trade name: MCP sodium salt), benzoic acid type of dimethyl-tetrachloroterephthalate (trade name: Ductal), phenol type of sodium pentachloro phenoxide (trade name: PCP), diphenyl ethers of 2,4-dichlorophenyl-p-nitro-phenyl ether (trade name: Nip), p-nitrophenyl-2,4,6-trichlorophenyl ether (trade name: MO) and p-nitrophenyl-m-tolyl ether, acid amide type of 3',4'-dichloropropionanilide (trade name: Stam), urea types such as 3-(3,4-dichlorophenyl)-1,1-dimethyl urea (trade name: Carmex D) and 3-(3,4-dichlorophenyl)-1-methoxy-1-methyl urea (trade name: Afaron), dinitroanilines such as α,α,α-trifluoro-2,6-dinitro-N,N-dipropyl-p-toluidine (trade name: Trefanocide), N-butyl-N-ethyl-α,α,α-trifluoro-2,6-dinitro-p-toluidine (trade name: Vanafin) and N-(1-ethylpropyl)-3,4-dimethyl-2,6-dinitroaniline (pendimethalin), nitriles such as 4-cyano-2,6-diiodophenyloctoate (trade name: Altinol) and 2,6-dichlorothiobenzamide (trade name: Tricide), S-triazines such as 2-chloro-4,6-bis(ethylamino)-1,3,5-triazine (trade name: Simazine) and 2-ethylamino-4-propylamino-6-methylthio-1,3,5-triazine (trade name: Gezapax), and diazines such as 3-(o-tolyloxy)pyridazine (trade name: Kusakiller), 5-bromo-3-butyl-6-methyluracil (trade name: Hyper X) and 5-amino-4-chloro-2-phenyl-3(2H)-pyridazinone (trade name: Lenapack).

Among the above compounds, the organic phosphorus compounds are preferable because the tendency of coloring in the dissolving process is low and the stability is good.

In general practice, 0.01 to 500 parts by weight of the diarylalkane as represented by the formula [I] is used to 1 part by weight of the active component. For example, in a solid composition or a suspension composition, the quantity of diarylalkane is preferably in the range of 0.1 to 10 parts by weight relative to one part by weight of the active component. In an oily composition, the diaryl-alkane is used in an amount of 0.1 to 500 parts by weight relative to one part by weight of the active component.

The pesticidal composition of the present invention may be in any known form such as emulsion, oily composition, solid composition including powder and granules, and smoking or fumigating composition.

In the preparation of the emulsion, the kind of emulsion is not especially limited but any of conventionally known emulsifying method can be employed. For example, the emulsion is prepared by emulsifying the solution of an effective component into water using an anionic surface-active agent such as alkylnaphthalene sulfonate, dodecylbenzene sulfonate or dialkylsulfosuccinate, or nonionic surface-active agent such as polyoxyalkylene ether, polyoxyalkylene sorbitan alkylate or polyoxyalkylene block polymer.

It is possible to add anti-oxidizing agent, ultraviolet light absorber or anti-gelling agent to the above emulsion. Furthermore, in the use of a organic phosphorus component, anti-decomposition agent can be added.

In the preparation of granular composition, (1) wet-type granulating method (extrusion granulation), (2) granulation-adsorption method and (3) surface-coating method are employed. When the pesticidal composition is used, it is diluted with water and then the dilution is spread or sprayed.

(1) In the wet-type granulating method, the composition of the present invention prepared by dissolving an effective component, binder and dispersing agent are added to inorganic carrier such as clay, bentonite or calcium carbonate and the mixture is then kneaded and extruded through a screen of appropriate mesh size to obtain granular product.

(2) In the granulation-adsorption, the composition of the present invention prepared by dissolving an effective component is mixed or sprayed to a carrier having adsorptive property so as to be adsorbed uniformly. The adsorptive carrier is exemplified by the powder which is obtained by pulverizing natural minerals such as bentonite, pumice, sintered diatomaceous earth and zeolite and granules of carrier which are formed by extrusion-granulation method.

(3) The surface coating method is suitable for a volatile or unstable effective component. The composition of the present invention prepared by dissolving an effective component is mixed into a carrier such as granular pumice or granular calcium carbonate, during which an oil absorbent such as white carbon is added to the mixture. The effective component in liquid state is absorbed by the oil absorbent and supported by the carrier to obtain the granules in which the carrier particles are coated with the effective component. If desired, the coating film is reinforced by adding a synthetic resin such as polyvinyl alcohol or sodium salt of carboxymethyl cellulose. Furthermore, a dispersing agent of sodium alkylbenzene sulfonate or sodium polyacrylate may be added. The thus prepared composition is used by mixing with water and applying by spreading or spraying.

The granular-powder composition and powder composition can be prepared likewise and used in the like manner as the above.

The flowable composition (sol or concentrated suspension) is prepared through the process such that a surface-active agent and diarylalkane of the formula [I] are mixed with and adsorbed by powdered effective component. After that, the mixture is suspended in water. When it is used, it is diluted with water and spread or sprayed.

In the smoking or fumigating composition, an effective component such as insecticide is added to a base material for heating or burning. It is used for pesticidal operation in which the effective component is volatilized by the heat from the base material or heat of combustion. For example, a porous carrier such as pulp is impregnated with the composition of the present invention that is prepared by dissolving an effective component, or the composition is formed into a solid preparation. This product is brought into contact with a heating element or is burnt to vaporize the effective component. Because the boiling point of the diarylalkane of the foregoing formula [I] is high, the pesticidal component can be vaporized effectively.

The pesticidal compositions to noxious organisms according to the present invention are classified as follows in view of their purposes of uses, treating methods and functions.

(i) Insecticide

In the classification in view of ingestion route (function) into the bodies of insects, the insecticide may comprise an oral administration agent which is taken into the body of an insect through its mouth; a contacting agent which is taken into the body of an insect when it is brought into contact with the epidermis; a fumigating agent which is taken into the insect's body through spiracles; an osmotic agent which is taken into the body of plants by osmosis from their roots, stems or leaves and the agent produces its effect when the plant or its sap is taken by an insect.

In the classification according to the modes of treatment, the insecticide may comprise a spreading agent which is spread to the stems and leaves of farm products to kill noxious insects; and a soil conditioning agent which is manured to the soil to kill the insect to injure roots or the soil conditioning agent is absorbed from roots and it is transferred to the upper part of a plant and that part of the plant containing the effective component is taken by insects to be killed.

Besides the above common pesticidal composition, the composition may comprise an insect attractant which induces insects, and a chemical pesticide which is obnoxious to insects (Kirk-Othmer Encyclopedia of Chemical Technology, 3rd ed. Supplement Volume, "Repellents"); and a chemical infertilizer which make insects infertile.

The insecticides are exemplified by pyrethroid type, organic phosphorus type, carbamate type and organic chlorine type (Kirk-Othmer Encyclopedia of Chemical Technology, 3rd ed. Vol. 13, "Insect Control Technology").

(ii) Sterilizer

There are several sterilizers such as a spreading composition which is spread to the stems and leaves of farm products to avoid the damages caused by blight or other plant diseases; soil conditioning agent which is manured to the soil to kill the pathogenic bacteria or is absorbed from roots and it is transferred by osmotic action to the upper part of plants, at which the sterilizing effect is produced; seed conditioning agent which is used for sterilizing seeds; water surface treating agent which is spread to water surface and it is transferred to the parts of rice plants above the water surface to produce sterilizing effect.

Exemplified as the sterilizing agents are azole type, amine type, benzimidazol type, dithiocarbamate type, dicarboxyimide type, organic phosphorus type, carboxyamide type, phenylamide type, antibiotics, organic chlorine type agents (Kirk-Othmer Encyclopedia of Chemical Technology, 3rd ed., Vil. 11, "Fungicides, Agricultural").

(iii) Herbicides

According to the purpose of use, there are a selective herbicide which does not produce any function to farm products (gives no damage) and kills weeds and a non-selective herbicide which is used to treat land other than farm or farm before seeding to avoid weeds.

According to the method of treatment, there are soil treating agent which is manured to the soil before seeding, transplanting or sprouting to avoid weeds and stalk and leaf treating agent which is applied to plants after sprouting.

The herbicides are exemplified by sulfonyl urea type, imidazolinone type, organic phosphorus type, diphenyl ether aryloxyphenoxy propionate type, cyclohexadione type, triazine type, urea type, amide type, aryloxy type, carbamate type and dinitroaniline type (Kirk-Othmer Encyclopedia of Chemical Technology, 3rd ed., Vol. 12, "Herbicides").

(iv) Plant Growth Regulator

This agent controls the physiological function of plants.

(v) Acaricide and Formicide (vi) Nematicide (vii) Rodenticide

The pesticidal composition of the present invention can be applied to any of the above purposes of chemical agents.

The above-mentioned pesticidal composition of diarylalkane of the formula [I] and effective pesticidal component is excellent in high flash point, no noxious odor, and the stability of the effective pesticidal component.

The present invention will be described in more detail with reference to examples and comparative examples.

<Preparation Example 1>

Reaction was carried out by blowing butene-1 into a mixture of diphenylmethane, 1,1-diphenylethane and 1,2-diphenylethane at a temperature of 160° C. in the presence of silica-alumina catalyst (trade name: IS-28, made by Shokubai Kasei Kogyo K. K.) to obtain a mixture of 55 wt. % of sec-butyldiphenylmethane, 26 wt. % of sec-butyl-1,1-diphenyl-ethane and 19 wt. % of sec-butyl-1,2-diphenylethane. The boiling point of the mixture was 304°–315° C. and the flash point thereof was 168° C. This reaction product is called as diarylalkane 1 (hereinafter referred to as "DAA1") and the physical properties of which are shown in the following Table 1.

<Preparation Example 2>

Using the same catalyst as that of Preparation Example 1, reaction was carried out with butene-1 and diphenylmethane to obtain sec-butyldiphenylmethane of 96 wt. % purity. The boiling point of the reaction product was 301° to 309° C. and the flash point thereof was 162° C. This reaction product is called as diarylalkane 2 (hereinafter referred to as "DAA2") and the physical properties thereof are shown in the following Table 1.

<Comparative Solvent>

The phenylxylylethane (trade name: SAS-296, made by Nippon Petrochemicals Co., Ltd., hereinafter referred to as "PXE") has hitherto been used for pesticidal compositions to noxious organisms. The physical properties of PXE are shown in the following Table 1.

It is understood that DAA1 and DAA2 used in the present invention have higher boiling points and flash points as compared with those of PXE.

TABLE 1

Physical Properties of Diarylalkanes

| Items | DAA1 | DAA2 | PXE |
|---|---|---|---|
| Distillation Range (°C.) | | | |
| Initial Boiling Point | 303 | 301 | 292 |
| 50% Point | 309 | 305 | 296 |
| End point | 316 | 309 | 303 |
| Flash Point (°C.) | 166 | 162 | 152 |

In order to compare the degrees of smell of above substances, 10 ml of each sample was put in a 100 ml receptacle. A comparative test on the intensity of smell was carried out by 50 persons of test panels including 15 women panels.

In the estimation concerning 3 kinds of test samples, the weakest smell was represented as 1 and the strongest smell was represented as 3. The average values and 95% confidence limits were calculated, the results of which are shown in FIG. 1.

From the above results, it was understood that there exist large significant differences between the values of both DAA1 and DAA2 and that of the Comparative Solvent PXE and that the smell of former group is quite small than that of the latter.

<Examples 1 and 2 and Comparative Example>

In each example, an oily composition containing 0.5 wt. % effective component was prepared by mixing with stirring the above-mentioned substances and the following effective components. The smell, stability of composition and coloring were determined with regard to the obtained oily composition just after the preparation and those after 3 years, by the following methods. The results are shown in the following Table 2.

[Pesticidal Components]
A. Organic Phosphorus Types
  (Main utility is indicated in brackets)
  (1) Sumithion: O,O-Dimethyl-O-(3-methyl-4-nitrophenyl)-thiophosphate (insecticide)
  (2) Diazinon: O,O-Diethyl-O-(2-isopropyl-4-methyl-6-pyrimidinyl)phosphorothioate (insecticide)
  (3) DDVP: O,O-Dimethyl-O-(2,2-dichlorovinyl) phosphate (insecticide)
B. Organic Chlorine Type
  TPN: Tetrachlorophthalonitrile (germicide)
C. Dinitroaniline Type
  Pendimethalin: N-(1-ethylpropyl)-3,4-dimethyl-2,6-dinitroaniline (herbicide)

[Estimation of Smell]
Each sample was spread using a sprayer and after a certain period of time, remaining smell was evaluated according to the following standard.

The results of test were indicated with the round off average of the scores of 5 test panels.

1: Hardly felt
2: Slightly felt
3: Felt really
4: Felt strongly
5: Felt very strongly

[Stability of Composition]
The content of effective component in a sample was determined and, after 3 years, the ratio of decomposition was calculated.

[Coloring Test]
The degree of coloring of sample was determined by naked eyes according to the following standards.

1: Scarcely colored
2: Slightly colored
3: Colored substantially
4: Colored strongly
5: Colored very strongly

TABLE 2

Smell, Stability and Coloring of Oily Composition

| DAA + Effective Comp. | Smell | | Stability (Ratio of Decomposition After 3 Years) | Coloring | |
|---|---|---|---|---|---|
| | Immediate | After 3 Years | | Immediate | After 3 Years |
| Example 1 | | | | | |
| DAA1 + Sumithion | 1 | 1 | 3 | 1 | 1 |
| DAA1 + Diazinon | 1 | 1 | 8 | 1 | 1 |
| DAA1 + DDVP | 1 | 1 | 9 | 1 | 1 |
| DAA1 + TPN | 1 | 1 | 8 | 1 | 1 |
| DAA1 + Pendimethalin | 1 | 1 | 11 | 1 | 1 |
| Example 2 | | | | | |
| DAA2 + Sumithion | 1 | 1 | 1 | 1 | 1 |
| DAA2 + Diazinon | 1 | 1 | 7 | 1 | 1 |
| DAA2 + DDVP | 1 | 1 | 9 | 1 | 1 |
| DAA2 + TPN | 1 | 1 | 7 | 1 | 1 |
| DAA2 + Pendimethalin | 1 | 1 | 10 | 1 | 1 |
| Comparative Example | | | | | |
| PXE + Sumithion | 2 | 2 | 4 | 1 | 1 |
| PXE + Diazinon | 2 | 2 | 9 | 1 | 1 |
| PXE + DDVP | 2 | 2 | 11 | 1 | 1 |
| PXE + TPN | 2 | 2 | 9 | 1 | 1 |
| PXE + Pendimethalin | 2 | 2 | 15 | 1 | 1 |

In order to confirm the effect as an insecticide and as a herbicide, the following test was carried out.

[Effect as Insecticide]

An effective component of diazinon was dissolved into DAA1 as prepared in the foregoing Preparation Example 1 to obtain an oily composition containing 1 wt. % of the effective component.

A branch of peach tree which was infested with a large number of cockchafer, was put into a 500 ml beaker. The oily composition as prepared in the above process was sprayed into the beaker with a spray gun.

As a result of observation, it was understood that their death rate was more than 90%.

[Effect as Herbicide]

An effective component of pendimethalin was dissolved into DAA1 as prepared in the foregoing Preparation Example 1 to obtain oily composition containing 30 wt. % of the effective component.

100 part by weight of pumice particles of 60 mesh in average was impregnated with 4 parts by weight of this oily composition to obtain a solid composition containing 1.2 wt. % of the effective component.

Sand was put on the bottom of a pot having horizontal dimensions of 10 cm×10 cm to form a 2 cm depth layer of the sand and farm soil of 10 cm in height was put on the layer of the sand. After that, seeds of crabgrass were sown in 1 cm depth.

Then, the above solid composition containing 1 mg of the effective component was spread evenly in the pot. By supplying water, the water content in the soil in pot was adjusted to about 15% and the growth of the crabgrass was observed for 35 days. As a result, the grass was completely withered after 35 days.

EFFECT OF THE INVENTION (1) The diarylalkane used in the present invention has sufficient dissolving power to dissolve a necessary quantity of the effective component of the pesticidal composition.

(2) The diarylalkane used in the present invention does hardly cause the decomposition or deterioration of the effective component when it is dissolved and the pesticidal effect is not deteriorated with the passage of time. Especially, when it is used in the form of solid preparation, the durability of pesticidal effect is important. If the diarylalkane of the present invention is used, the properties of pesticidal composition can be kept stable and the full effect can be kept for a long period of time. In addition, composition coloring scarcely occurs after dissolution and storing.

(3) The stability of emulsion is important when the diarylalkane is used in the form of an emulsion. The diarylalkane used in the present invention is preferable because it hardly spoils the stability of the emulsion. For example, when the stability of emulsion is not good, the emulsion is destroyed and effective component is deposited. The phenomenon like this is not desirable because it causes a harmful effect and the lowers the pesticidal effect. When a solvent of a high dissolving power is used, the emulsion stability is liable to be lost.

(4) The diarylalkanes used in the present invention have high flash points and high boiling points, so that the compositions of the invention are safer to fire than others.

(5) The diarylalkanes used in the present invention scarcely produce unpleasant smell and are almost odorless.

(6) The diarylalkanes used in the present invention are safe compounds, so that they have no harmful effect by smell and stimulation.

(7) The diarylalkane as represented by the foregoing formula [I] used for the pesticidal composition to noxious organisms in the first object of the invention is safe relative to fire because the flash point is high and the boiling point is also high, so that it does not produce unpleasant smell and is almost odorless.

(8) The butyl diphenylmethane, butyl-1,1-diphenylethane and butyl-1,2-diphenylethane used for the pesticidal composition in the second object of the invention have improved smell and the flash points are high, in addition, the dissolving powers to the effective component are large, so that the obtained composition is stable.

(9) The mixture of 20 to 80 wt. % of butyl diphenylmethane, 5 to 50 wt. % of butyl-1,1-diphenylethane and 5 to 50 wt. % of butyl-1,2-diphenylethane which is used for the pesticidal composition in the third object of the invention has improved pour point and it is advantageous in smell, stability of effective component and low coloring.

(10) The butyldiphenylmethane used for the pesticidal composition in the fourth object of the invention is further excellent in dissolving power to the effective component and it is also excellent in smell, stability of effective component and low coloring.

What is claimed is:

1. A pesticidal composition which comprises an active component which kills or repels noxious organisms and a diarylalkane as represented by the following formula [I]¹

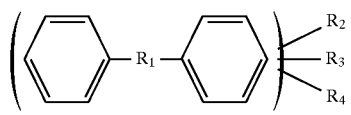

wherein $R_1$ is a bivalent radical which is formed from methane or ethane, each of $R_2$ and $R_3$ is a hydrogen atom or an alkyl group having 3 or 4 carbon atoms, $R_4$ is an alkyl group having 3 or 4 carbon atoms, and the groups $R_2$, $R_3$ and $R_4$ can be the same or different ones, and wherein said diarylalkane is present in said composition in an amount of from about 0.01 to about 500 parts by weight based on 1 part by weight of said active component, and said composition is substantially free of noxious odor.

2. The pesticidal composition as claimed in claim 1, wherein said diarylalkane is one member selected from the group consisting of butyl diphenylmethane, butyl-1,1-diphenylethane, and butyl-1,2-diphenyl-ethane.

3. The pesticidal composition as claimed in claim 1, wherein said diarylalkane is a mixture of 20 to 80 wt. % of butyl diphenylmethane, 5 to 50 wt. % of butyl-1,1-diphenylethane and 5 to 50 wt. % of butyl-1,2-diphenylethane.

4. The pesticidal composition as claimed in claim 1, wherein said diarylalkane contains more than 80 wt. % of butyl.

5. A pesticidal composition as claimed in claim 1 wherein said diarylalkane comprises at least one member selected from the group consisting of propyl diphenylmethane, propyl-1,1-diphenylethane, propyl-1,2-diphenylethane, butyl diphenylmethane, butyl-1,1-diphenylethane, butyl-1,2-diphenylethane, dipropyl diphenylmethane, dipropyl-1,1-diphenylethane, dipropyl-1,2-diphenylethane, dibutyl diphenylmethane, dibutyl-1,1 -diphenylethane and dibutyl-1,2-diphenylethane.

6. A pesticidal composition as claimed in claim 1, wherein said composition comprises a solid composition and said diarylalkane is present in said composition in an amount of from about 0.1 to about 10 parts by weight based on 1 part by weight of said active component.

7. A pesticidal composition as claimed in claim 1, wherein said composition comprises a suspension composition and said diarylalkane is present in said composition in an amount of from about 0.1 to about 10 parts by weight based on 1 part by weight of said active component.

8. A pesticidal composition as claimed in claim 1, wherein said composition comprises a liquid and said diarylalkane is present in said composition in an amount of from about 0.1 to about 500 parts by weight based on 1 part by weight of said active component.

9. A pesticidal composition as claimed in claim 1, wherein said active component comprises at least one component selected from the group consisting of insectides and industrial microbicides.

10. A pesticidal composition as claimed in claim 1, wherein said active component comprises at least one component selected from the group consisting of organic phosphorus components, carbamate components, organic chlorine compound components, phenoxide components, benzoic acid components, phenol components, urea components, dinitroaniline components, nitrile components, S-triazine components and diazine components.

11. A pesticidal composition as claimed in claim 1, wherein said diarylalkane has a flash point of 152° C. or higher.

12. A pesticidal composition as claimed in claim 1, wherein said active component comprises at least one component selected from the group consisting of O,O-dimethyl-O-(3-methyl-4-nitrophenyl) thiophosphate, ethyl-p-nitrophenyl-phenylphosphorothionate, diethyl-(2,4-dichlorophenyl) thiophosphate, dimethyl-4-methylthio-m-tolylphosphorothionate, O,O-diethyl-O-(2-isopropyl-4-methyl-6-pyrimidinyl) phosphorothioate, O-ethyl-diphenyldithio phosphate, S-benzyl-ethyl-phenylphosphonothiolate, tetrachlorovinphos, phoxim, O,O-dimethyl-O-(2,2-dichlorovinyl) phosphate, 1-naphthyl-N-methylcarbamate, 2-ethylthio-methyl) phenyl-methylcarbamate, 2-butylphenyl-N-methylcarbamate, O,O-diethyl-O-3,5,6-trichloro-2-pyridyl phosphorothioate, tetrachloroisophthalonitrile, 4,5,6,7-tetrachlorophthalide, N-tetrachloroethylthiotetrahydrophtalimide, chlorobenzylate, O,O-diethyl phthalimid methyldithiophosphate, etofenprox, tripropyl cyanate, sodium-2,4-dichlorophenoxyacetate, sodium [(4-chloro-tolyl)oxy]acetate, dimethyl-tetrachloroterephthalate, sodium pentachloro phenoxide, diphenyl ethers of 2,4-dichlorophenyl-p-nitrophenyl ether, p-nitrophenyl-2,4,6-trichlorophenyl ether, p-nitrophenyl-m-tolylether, 3',4'-dichloropropionanilide, 3-(3,4-dichlorophenyl)-1,1-dimethyl urea, 3 -(3,4-dichlorophenyl)- 1-methyl urea, α, α, α-trifluoro-2,6-dinitro-N,N-dipropyl-p-toluidine, N-butyl-N-ethyl-α, α, α-trifluoro-2,6-dinitro-p-toluidine, N-(1-ethylpropyl)-3 ,4-dimethyl-2,6-dinitroaniline, 4-cyano-2,6-diiodophenyloctoate, 2,6-dichlorothiobenzamide, 2-chloro-4,6-bis(ethylamino)- 1,3,5-triazine, 2-ethylamino-4-propylamino-6-methylthio- 1,3,5-triazine, 3 -(0-tolyloxy) pyridazine, 5-bromo-3 -butyl-6-methyluracil, and 5-amino-4-chloro-2-phenyl-3 (2H)-pyridazinone.

* * * * *